US00PP17470P2

(12) United States Plant Patent
Schlueter

(10) Patent No.: US PP17,470 P2
(45) Date of Patent: Mar. 6, 2007

(54) ***HIBISCUS ROSA-SINENSIS* PLANT NAMED 'ISLAND MAGIC'**

(50) Latin Name: *Hibiscus rosa-sinensis*
Varietal Denomination: ISLAND MAGIC

(75) Inventor: Barry Schlueter, Houston, TX (US)

(73) Assignee: Hines Nurseries, Inc., Irvine, CA (US)

( * ) Notice: Subject to any disclaimer, the term of this patent is extended or adjusted under 35 U.S.C. 154(b) by 5 days.

(21) Appl. No.: 11/207,516

(22) Filed: Aug. 19, 2005

(51) Int. Cl.
*A01H 5/00* (2006.01)

(52) U.S. Cl. ..... Plt./257

(58) Field of Classification Search ..... Plt./257
See application file for complete search history.

*Primary Examiner*—Kent Bell
(74) *Attorney, Agent, or Firm*—Christie, Parker & Hale, LLP

(57) ABSTRACT

A new and distinct cultivar of *Hibiscus* plant named 'ISLAND MAGIC', characterized by a large multicolored flower with a red center, radiating out to shades of orange-red with a yellow halo around the edges. 'ISLAND MAGIC' is a free flowering plant with an upright, compact habit, and glossy, dark green foliage.

4 Drawing Sheets

Botanical classification: *Hibiscus rosa-sinensis* 'ISLAND MAGIC'.

Varietal denomination: The new plant has the varietal denomination 'ISLAND MAGIC'.

BACKGROUND OF THE INVENTION

The present invention relates to a new and distinct cultivar of *Hibiscus,* botanically known as *Hibiscus rosa-sinensis* and hereinafter referred to by the cultivar name 'ISLAND MAGIC'.

The genus *Hibiscus* comprises about 250 species of herbs, shrubs and trees in warm temperate and tropical regions; with leaves usually simple, mostly palmately veined, lobed or parted; flowers are mostly solitary in the leaf axils but sometimes in racemes, corymbs or panicles. *Hibiscus* is included in the family Malvaceae, which comprises about 95 genera of herbs, shrubs and trees originating in tropical and temperate regions. *Hibiscus rosa-sinensis* is a glabrate shrub, seldom over 8 feet tall in cultivation, but treelike to 15 feet or more in tropical regions. Leaves grow to 6-inches in length, and are ovate, usually serrate, mostly glossy green. Flowers are solitary in upper leaf axils.

The new *Hibiscus* is a product of a planned breeding program conducted by the Inventor in Webster, Tex. The objective of the program was to create new *Hibiscus* selections with improved bloom quality, color and floriferousness. A further objective was to produce plants that can be commercially produced on their own root systems, with improved plant habit, with regard to vigor and postproduction longevity.

The new variety was discovered in a controlled breeding program of *Hibiscus rosa-sinensis* and differs from its parents and other known cultivars of *Hibiscus rosa-sinensis* by the following characteristics in combination:

1. Upright, compact symmetrical plant habit that is suitable for container production;
2. Healthy dark green foliage;
3. Vigorous growth habit;

4. Large ruffled multicolored flower with a red center, radiating to shades of orange-red with a yellow halo around the edges; and
5. Free flowering.

SUMMARY OF THE INVENTION

The cultivar 'ISLAND MAGIC' has not been observed under all possible environmental conditions. The phenotype may vary somewhat with variations in environment such as temperature, light intensity, nutrition and water status without, however, any variance in genotype.

The following traits have been repeatedly observed and are determined to be unique characteristics of 'ISLAND MAGIC'. These characteristics in combination distinguish 'ISLAND MAGIC' as a new and distinct cultivar:

1. Upright, compact symmetrical plant habit that is suitable for container production.
2. Healthy dark green foliage.
3. Vigorous growth habit.
4. Large ruffled multicolored flower with a red center, radiating to shades of orange-red with a yellow halo around the edges.
5. Free flowering.

Asexual reproduction of the new variety by stem cuttings, performed in Webster, Tex. and Houston, Tex., have confirmed that the distinctive characteristics of the new variety are stable and transmitted to succeeding generations, and the new variety reproduces true to type.

COMPARISON WITH PARENTS AND OTHER CULTIVARS

'ISLAND MAGIC' is distinguished from its female parent 'Heartbreak Hotel' (not patented) by its flower color and size. The flower color of 'Heartbreak Hotel' is mahogany red with yellow spots, and the size of the flower is often 2 to 5 cm smaller in diameter than that of 'ISLAND MAGIC'. 'ISLAND MAGIC' is distinguished from its male parent 'Jason Blue' (not patented) in the flower color, 'Jason Blue' having an orange-yellow flower with a silvery blue eye.

The closest commercial cultivar to 'ISLAND MAGIC' known to the Inventor is 'Orange Magic' (not patented). However, in side-by-side comparisons conducted in Webster, Tex., plants of 'ISLAND MAGIC' differ from plants of 'Orange Magic' in the following characteristics:

1. Flowers of the new *hibiscus* are larger than flowers of the cultivar 'Orange Magic'.
2. Plants of the new *Hibiscus* are easier to clone via rooting than plants of the cultivar 'Orange Magic'; and
3. Plants of the new *Hibiscus* are more floriferous than are plants of the cultivar 'Orange Magic'.

BRIEF DESCRIPTION OF THE DRAWINGS

The accompanying illustrations show a specimen of the new cultivar in a photographic illustration as true to color as is reasonably possible to make in an illustration of this character. Color values in the illustrations may differ slightly from the color values cited in the detailed botanical description, which accurately describes the actual colors of the new *Hibiscus*.

DETAILED DESCRIPTION OF THE INVENTION

Figure 1:
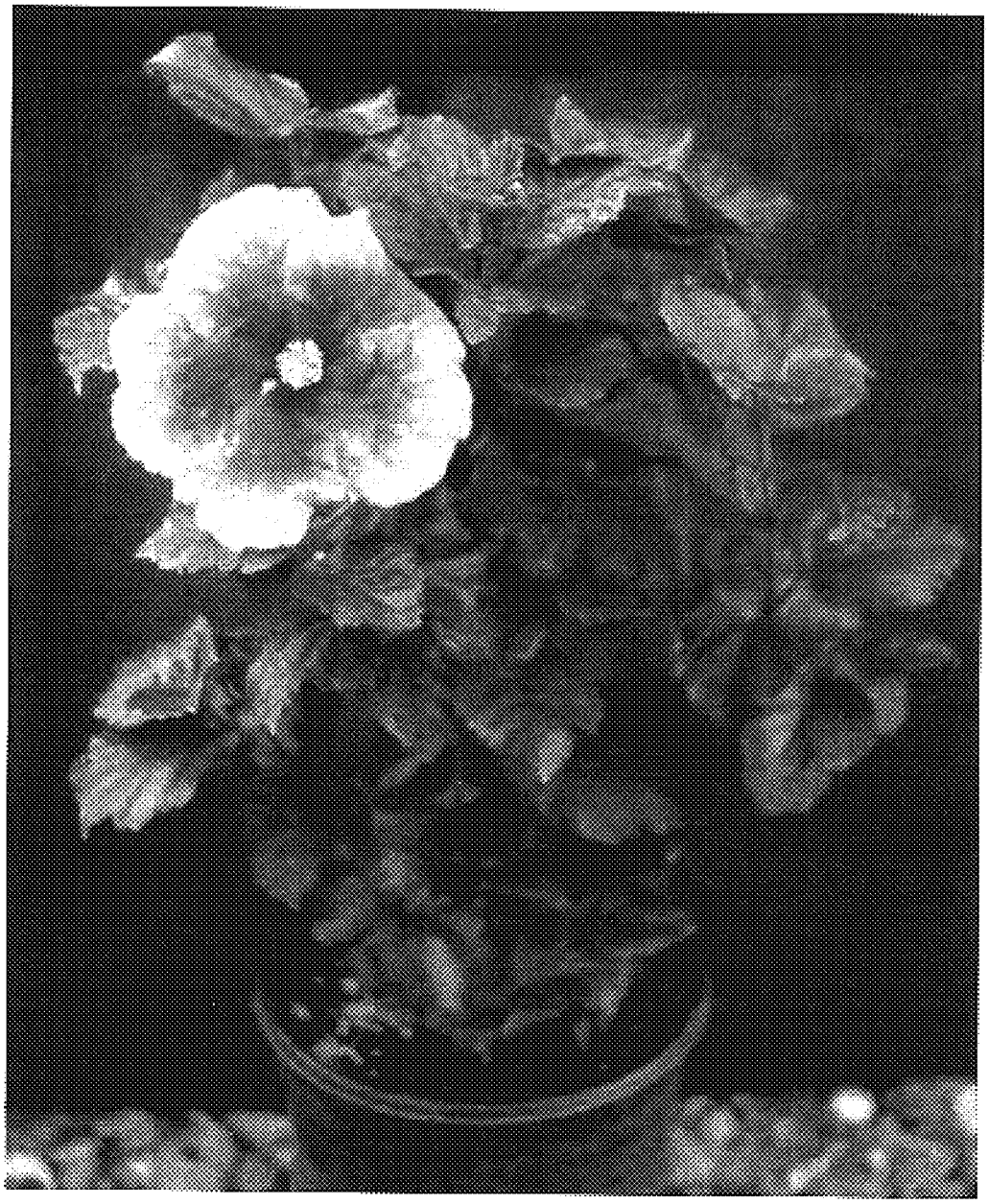
FIG. 1 illustrates a side perspective view of a typical plant of 'ISLAND MAGIC'.
Figure 2:
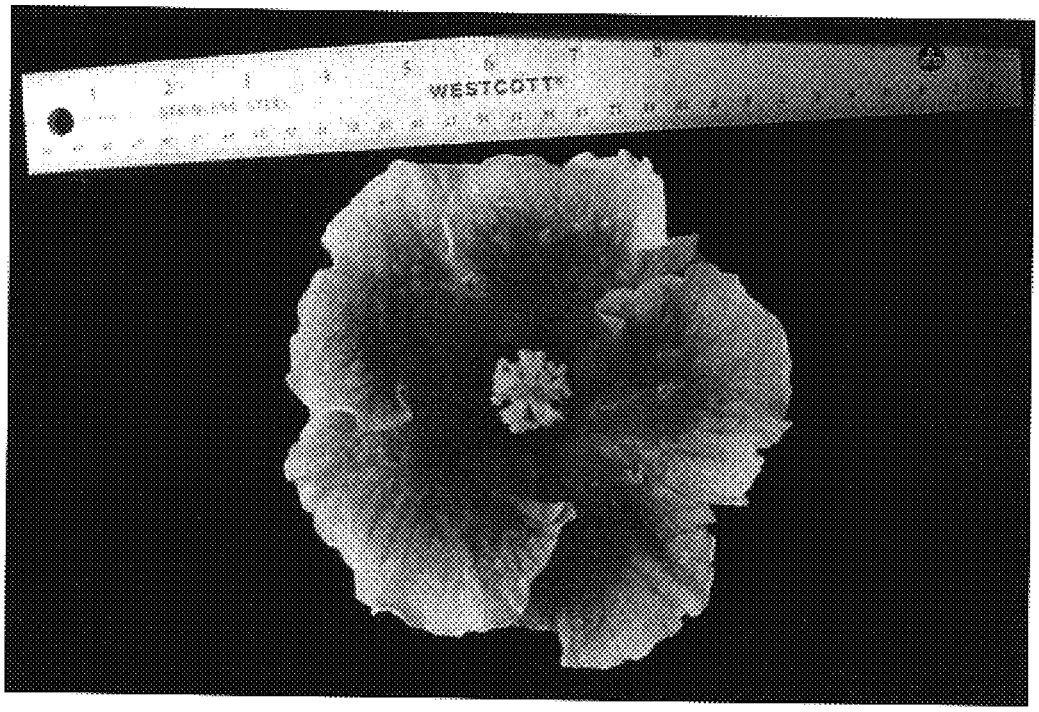
FIG. 2 illustrates the scale of a typical flower of 'ISLAND MAGIC'.
Figure 3:
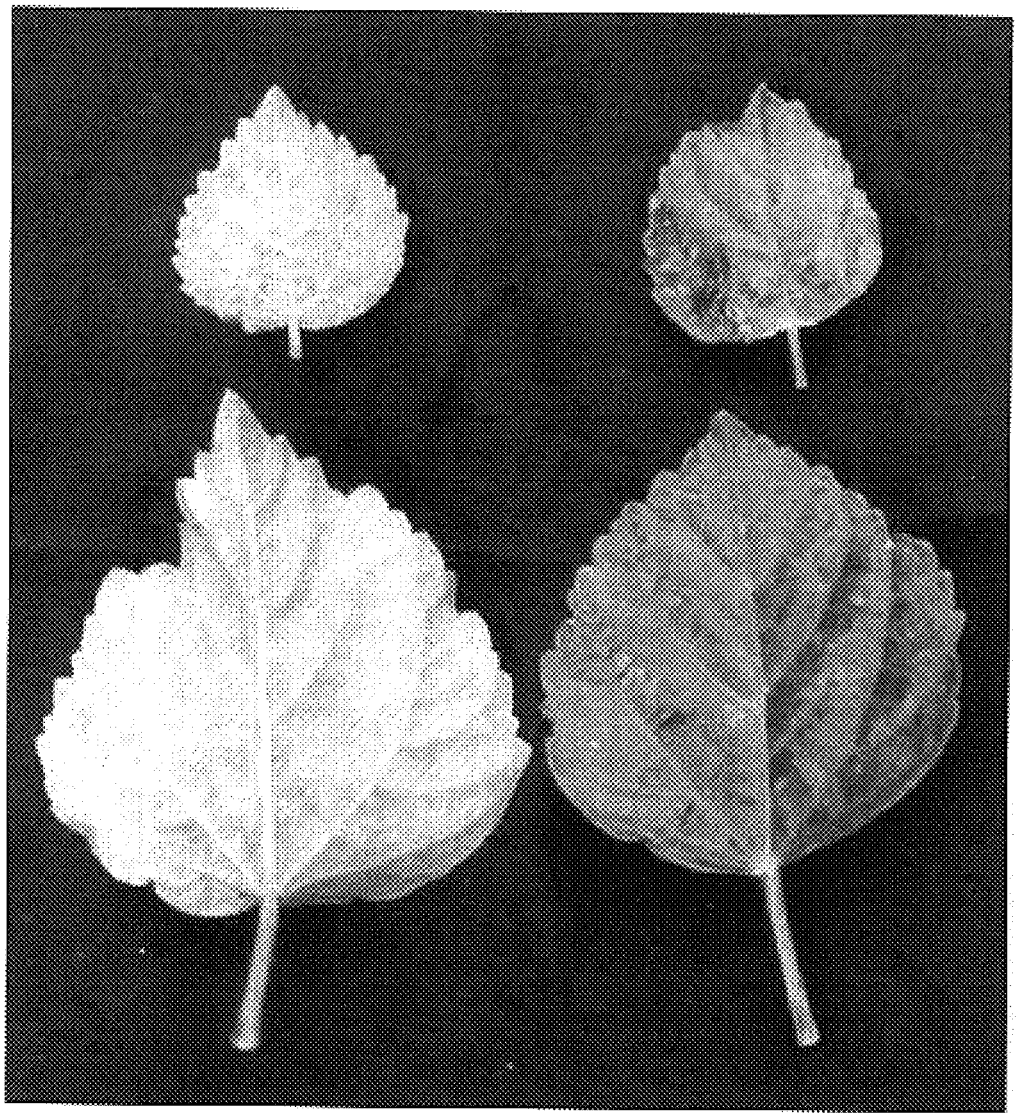
FIG. 3 illustrates the typical young to mature foliage of 'ISLAND MAGIC'; the abaxial and adaxial surfaces are shown at each stage.
Figure 4:
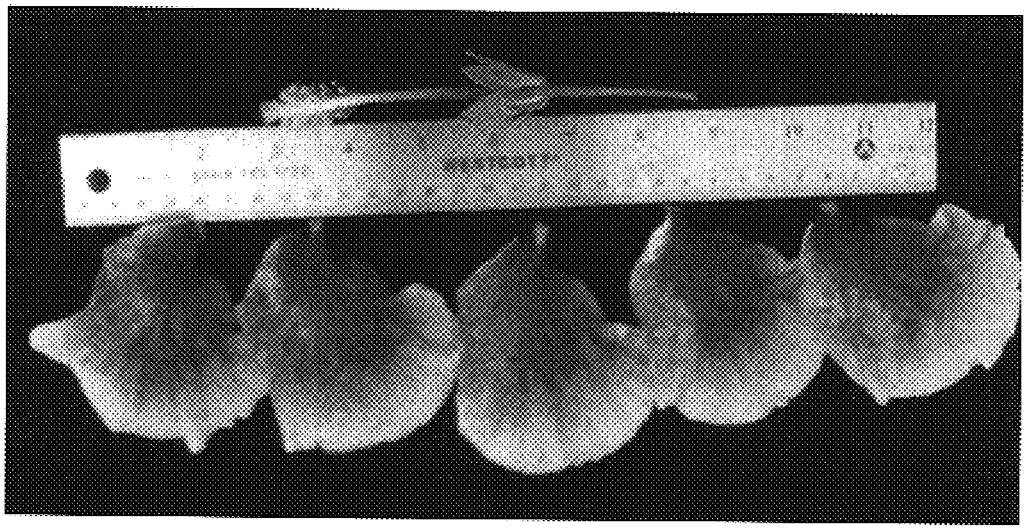
FIG. 4 illustrates a dissected flower of 'ISLAND MAGIC', including shape and size of petals and characteristics of the reproductive structures.

'ISLAND MAGIC' has not been observed under all possible environmental, cultural and light conditions. The following observations and descriptions are of plants grown in Fulshear, Tex., in April 2005, under polypropylene shadecloth providing a 30 percent light reduction, and under conditions which closely approximate commercial production. Plants described were approximately one year old.

In this description, color references are to The Royal Horticultural Society Colour Chart (4th Edition) and terminology used in the color descriptions herein refers to plate numbers in this color chart. Phenotypic expression may vary with light intensity, cultural and environmental conditions.

Classification:

*Botanical.*—*Hibiscus rosa-sinensis* 'ISLAND MAGIC'.

*Parentage.*—Female or Seed Parent: *Hibiscus rosa-sinensis* 'Heartbreak Hotel'. Male or Pollen Parent: *Hibiscus rosa-sinensis* 'Jason Blue'.

*Propagation.*—By cuttings.

*Time to initiate rooting.*—Approximately 14 to 21 days at 21–24° C.

*Time to develop roots.*—Approximately 42 to 56 days at 21–24° C.

*Root description.*—Fine to medium; fibrous; freely branching.

Plant:

*Size.*—Height: Approximately 45–50 cm in a #2 pot (from soil level to top of flowers). Diameter/Spread: Approximately 40–45 cm in a #2 pot.

*Form and growth habit.*—Perennial, evergreen shrub; mostly upright and somewhat spreading.

*Branching.*—Freely branching, about 4 to 8 lateral branches develop after pinching. Lateral Branches: Approximately 20 cm long and 3 mm in diameter. Color: Young — 138B. Mature — grey brown 199C. Internode Length: Approximately 3 cm.

Leaf:

*Shape.*—Cordate. Apex: Acute. Base: Cordate.

*Leaf size.*—Approximately 9 cm long and 8.5 cm wide.

*Arrangement.*—Alternate, single, symmetrical.

*Margin.*—Crenate.

*Aspect.*—Undulate.

*Texture.*—Glabrous, shiny.

*Coloration.*—Young Foliage Upper side: Near Green Group 137A. Under side: Near Green Group 137C. Mature Foliage Upper side: Near Green Group 139A. Under side: Near Green Group N138B.

*Petioles.*—Size: Approximately 3 cm in length; approximately 3 mm in diameter. Coloration: Near Green Group 137B. Texture: Smooth.

Inflorescence:

*Bloom period.*—Typically year-round under subtropical and tropical conditions.

*Flower arrangement.*—Arranged singly at terminal leaf axils; free flowering with 3 to 4 flower buds and/or open flowers per terminal apex; flowers face upright and slightly outward.

*Flower appearance.*—Ruffled and multicolored with a dark red center, radiating to orange-red, ending with a yellow edge; flowers are open for about two days before closing; flowers persistent.

*Flower diameter.*—Approximately 16 cm.

*Flower depth.*—When placed on a horizontal plane, the flower extends 6 cm above the surface, with the ruffled petals extending 1.5–2.0 cm above the plane.

*Buds* (*just prior to showing color*).—Rate of Opening: Approximately 1 or 2 days, depending on temperature. Shape: Elliptic. Length: Approximately 3 cm. Diameter: Approximately 1 cm. Color: Near Green Group 137C.

*Fragrance.*—None noted.

*Petals.*—Number/Arrangement: Corolla consists of 5 overlapping petals. Shape: Spatulate with rounded apex. Size: Approximately 9 cm long and 9 cm wide. Margin: Entire, but wavy. Texture: Smooth. Base Descriptor: Oblique. Color Upper Surface: The eye or center is near Red Group 46A, transitioning outward to near Red Group between 42A and 42C; the outer edge is near Yellow Group 12B. Lower Surface: Majority of the lower surface is near Yellow Group 11C, with near Red Group 48C at the base of the petal.

*Sepals.*—Number/Arrangement: 5 sepals fused into a star-shaped calyx. Shape: Linear with acuminate apices. Margin: Entire. Color: Near Green Group 137C.

*Peduncles.*—Length: Approximately 4 cm. Diameter: Approximately 2 mm. Angle: Upright to about 45 degrees. Strength: Strong, flexible. Color: Near Green Group 138B.

Reproductive organs:

*Androecium.*—Stamens: Numerous; approximately 50. Stamen Length: Approximately 5 mm. Filament Color: Near White Group 155B. Anther Size: Approximately 1 mm long×1 mm wide. Pollen Amount: Abundant. Pollen Color: Near Yellow Group 6A.

*Gynoecium.*—Pistil Length: Approximately 8 cm. Stigma Appearance: Five, rounded. Stigma Diameter: Approximately 2 mm. Stigma Color: Near Orange Group N25A. Style Color: Lower two-thirds near Red Group 46A; upper one-third near White Group 155B. Seed Production: Has not been observed.

Pests/diseases: Resistance to known *Hibiscus* diseases had not been observed on plants grown under conditions approximating commercial practices.

What is claimed is:

1. A new *Hibiscus rosa-sinensis* plant named 'ISLAND MAGIC', substantially as shown and described.

* * * * *